(12) United States Patent
Schmidt et al.

(10) Patent No.: US 8,684,943 B2
(45) Date of Patent: Apr. 1, 2014

(54) MULTI PARAMETRIC CLASSFICATION OF CARDIOVASCULAR SOUND

(75) Inventors: Samuel Emil Schmidt, Aalborg (DK); Johannes Jan Struijk, Terndrup (DK); Claus Graff, Klarup (DK)

(73) Assignee: Acarix A/S, Lyngby (DK)

( * ) Notice: Subject to any disclaimer, the term of this patent is extended or adjusted under 35 U.S.C. 154(b) by 737 days.

(21) Appl. No.: 12/308,754

(22) PCT Filed: Jun. 26, 2007

(86) PCT No.: PCT/DK2007/000309
§ 371 (c)(1),
(2), (4) Date: Mar. 3, 2010

(87) PCT Pub. No.: WO2008/000259
PCT Pub. Date: Jan. 3, 2008

(65) Prior Publication Data
US 2010/0160807 A1    Jun. 24, 2010

(30) Foreign Application Priority Data
Jun. 26, 2006  (WO) ................ PCT/DK2006/000374

(51) Int. Cl.
*A61B 5/02*  (2006.01)
(52) U.S. Cl.
USPC ........... 600/528; 600/508; 600/509; 600/514; 600/515
(58) Field of Classification Search
USPC .................... 600/508–509, 514–515, 528
See application file for complete search history.

(56) References Cited

U.S. PATENT DOCUMENTS

| 5,036,857 | A | 8/1991 | Semmlow et al. |
| 6,053,872 | A | 4/2000 | Mohler |
| 2002/0099286 | A1 | 7/2002 | Sandler et al. |
| 2004/0260188 | A1 | 12/2004 | Syed et al. |
| 2005/0090755 | A1 | 4/2005 | Guion et al. |

FOREIGN PATENT DOCUMENTS

| DE | 37 32 122 | 4/1989 |
| JP | 3-503962 | 9/1991 |
| JP | 2005-296643 | 10/2005 |
| JP | 2006-505300 | 2/2006 |
| WO | WO 89/06932 | 8/1989 |
| WO | WO 03/088841 | 10/2003 |

OTHER PUBLICATIONS

Semmlow, J., et al., "Coronary Artery Disease—Correlates Between Diastolic Auditory Characteristics and Coronary Artery Stenoses," IEEE on Biomedical Engineering, vol. BME-30, No. 2, pp. 136-139, Feb. 1983.

(Continued)

*Primary Examiner* — Deborah Malamud
(74) *Attorney, Agent, or Firm* — Jacobson Holman PLLC

(57) ABSTRACT

A method, system, stethoscope and server for classifying a cardiovascular sound recorded from a living subject. The method comprises the steps of: identifying diastolic and/or systolic segments of the cardiovascular sound; dividing at least one of the identified diastolic and/or systolic segments into a number of sub-segments comprising at least a first sub-segment and at least a second sub-segment; extracting from the first sub-segment at least a first signal parameter characterizing a first property of the cardiovascular sound, extracting from the second sub-segment at least a second signal parameter characterizing a second property of the cardiovascular sound; and classifying the cardiovascular sound using the at least first signal parameter and the at least second signal parameter in a multivariate classification method.

25 Claims, 9 Drawing Sheets

(56) References Cited

OTHER PUBLICATIONS

Wang, P., et al., "Phonocardiographic Signal Analysis Method Using a Modified Hidden Markov Model," Biomedical Engineering, vol. 35, No. 3, pp. 367-374, Mar. 2007.

Brusco, M., et al., "Development of an Intelligent PDA-based Wearable Digital Phonocardiograph," IEEE on Engineering in Medicine and Biology 27th Annual Conference, pp. 3506-3509, Sep. 2005.

Durand, L., et al., "Digital Signal Processing of the Phonocardiogram: Review of the Most Recent Advancements," Critical Reviews in Biomedical Engineering, vol. 23, No. 3/4, pp. 163-219, 1995.

Haghighi-Mood, A., et al., "Time-Frequency Analysis of Systolic Murmurs," Proceedings of the 1997 IEE Colloquium on Time Frequency Analysis of Biomedical Signals, pp. 7-1, Jan. 29, 1997.

MULTI PARAMETRIC CLASSFICATION OF CARDIOVASCULAR SOUND

This is a national stage of PCT/DK2007/000309 filed Jun. 26, 2007 and published in English, which has a priority of Denmark No. PCT/DK2006/000374 filed Jun. 26, 2006, hereby incorporated by reference.

FIELD OF THE INVENTION

The present invention relates to methods and systems for classification of heart sounds recorded from a living subject into classes describing whether or not murmurs due to coronary artery stenosis are present in the heart sound.

BACKGROUND OF THE INVENTION

Coronary artery disease is the single most common cause of death from cardiovascular disease in the western world. The heart muscle receives its blood supply through the coronary arteries, and atherosclerosis is the most common pathophysiologic process occurring in the coronary arteries giving rise to coronary artery disease (CAD). Atherosclerosis is a process that builds up plaques within the artery, and the blood flow can therefore be reduced or even blocked by the plaque. The constantly working heart requires a continuous and efficient blood supply in order to work properly. Defects in the blood supply may be very severe and even fatal. Increasing degrees of luminal diameter reduction or stenosis of the coronary artery will first limit reserve flow, then reduce flow at rest and may finally totally occlude the vessel.

There is a need for measuring/detecting coronary artery stenosis for clinicians and other medical professionals to diagnose CAD. Once a diagnosis has been made a cure/treatment could be started.

Today several non-invasive techniques for measuring/detecting the severity of a stenosis or its presence inside a coronary artery exist. This can be done by magnetic resonance imaging (MRI), in vivo intravascular ultrasound (IVUS) or optical coherence tomography (OCT). However, the above-mentioned techniques are all rather complicated and expensive to use and therefore only patients with specific symptoms are offered such examinations. The consequence is that most patients have a critical stenosis when examined.

Clinicians and other medical professionals have long relied on auscultatory sounds such as cardiovascular sounds to aid in the detection and diagnosis of physiological conditions. For instance, a clinician may utilize a stethoscope to monitor and record heart sounds in order to detect heart valve diseases. Furthermore, the recorded heart sounds could be digitized, saved and stored as data files for later analysis. Devices have been developed that apply algorithms to electronically recorded auscultatory sounds. One example is an automated blood-pressure monitoring device. Other examples include analysis systems that attempt to automatically detect physiological conditions based on the analysis of auscultatory sounds. For instance, artificial neural networks have been discussed as one possible mechanism for analyzing auscultatory sounds and providing an automated diagnosis or suggested diagnosis. It is difficult to provide an automated device for classifying auscultatory sounds according to coronary stenosis using these conventional techniques, because it is very difficult to adapt these techniques to take account of the differences between persons. Two different persons would influence the auscultatory sounds differently and the auscultatory sounds from two patients could be different even though both persons suffer from coronary stenosis. Moreover, it is often difficult to implement the conventional techniques in a manner that may be applied in real-time or pseudo real-time to aid the clinician.

Many clinicians prefer to use a digital stethoscope to acquire auscultatory sounds because they are familiar with stethoscopes, but the quality of auscultatory sounds acquired with a digital stethoscope is very often poor compared to auscultatory sounds recorded by more advanced systems. The quality of such auscultatory sounds is often reduced because additional noise is introduced during the recording—e.g. due to friction between the microphone and the patient's chest or due to noise in the surroundings. Further, it is a very intimate situation when a clinician records an auscultatory sound using a stethoscope because the distance between the patient and the clinician is very small, and the consequence is that the auscultatory recording is very short. Therefore only a small amount of data suitable for performing an analysis of the coronary artery disease is acquired when using a stethoscope and the analyses performed by known techniques are therefore very often incorrect.

U.S. Pat. No. 5,036,857 discloses a method and a system for non-invasively detecting Coronary Artery Disease. The method comprises analyzing the diastolic heart sounds detected from a patient's chest cavity during the diastolic portion of the heart cycle in order to identify a low level auditory component associated with turbulent blood flow in partially occluded coronary arteries. These diastolic heart sounds are modelled using advanced signal processing techniques such as Autoregressive (AR), Autoregressive Moving Averaging (ARMA) and Eigenvector methods, so that the presence of such an auditory component may be reliably indicated. The system includes an acoustic transducer, a pulse sensor device, signal processor means and a diagnostic display. Additionally, the system includes a controller for automatically sequencing data collection, analysis and display stages, therefore requiring a minimum of operator interaction. This method and system analyzes the amount of noise in the diastolic segments, and diastolic segments with a large amount of noise are discarded and not used in the analysis of low level auditory components associated with turbulent blood flow in partially occluded coronary arteries. Therefore a large amount of diastolic segments need to be recorded in order to achieve a proper analysis, and the sound recording should therefore be very long or repeated many times. This is in many clinical situations not possible especially when using a digital stethoscope to record the heart sound.

OBJECT AND SUMMARY OF THE INVENTION

The object of the present invention is to solve the above-mentioned problems.

This is achieved by a method of classifying a cardiovascular sound recorded from a living subject; said method comprises the steps of:
  identifying diastolic and/or systolic segments of said cardiovascular sound;
  dividing at least one of said identified diastolic and/or systolic segments into a number of sub-segments comprising at least a first sub-segment and at least a second sub-segment;
  extracting from said first sub-segment at least a first signal parameter characterizing a first property of said cardiovascular sound, extracting from said second sub-segment at least a second signal parameter characterizing a second property of said cardiovascular sound;

classifying said cardiovascular sound using said at least first signal parameter and said at least second signal parameter in a multivariate classification method.

Hereby a very robust and simple method that only needs a small amount of cardiovascular sound in order to classify the sound is provided. The consequence is that cardiovascular sounds could be classified based on a short recording which is very convenient when the sounds have been recorded by a stethoscope. This is achieved because the diastolic and/or systolic segments of the cardiovascular sound are divided into sub-segments, and the cardiovascular sound is hereafter classified based on signal parameters extracted from at least two sub-segments from the same diastolic or systolic segment. The consequence is that classification of the cardiovascular signal could be based only on sub-segments with a good signal to noise ration; e.g. sub-segments with no friction or background noise. The sub-segments with a bad signal to noise ratio could therefore be discarded before classifying the cardiovascular sound. Hereby only a small amount of recorded cardiovascular sound is needed in order to achieve a correct classification because only a very small part of the recorded signal needs to be discarded due to noise. The cardiovascular sound related to turbulence comprises at least two components: a broad band component caused by turbulent blood flow colliding with the arterial wall and a narrow banded component related to the resonance frequency of the artery wall. Therefore different variables describing different properties are needed in order to perform a robust classification. The cardiovascular sound would further vary from person to person due to the persons' physical differences, e.g. bone structure, thickness of chest, amount of fat etc. The present invention eliminates this variation by using different signal parameters when classifying the cardiovascular sound. Some signal parameters could for instance from one person be used to significantly classify the cardiovascular sound, whereas the same signal parameters from a second person would not be suitable for a significant classification of the cardiovascular signal. However, in this situation other signal parameters could be used to classify the cardiovascular sound from the second person when using the method according to the present invention. Further, some signal parameters may be influenced by one kind of the differences between the persons and other signal parameters may be influenced by other kinds of differences. Therefore, choosing a number of different signal parameters would make the classification method more robust. The different signal parameters describe different characteristics of the cardiovascular sound and would therefore be uncorrelated and therefore provide different information of the cardiovascular sound. Different signal parameters could for instance be the time duration of the diastolic segment of the cardiovascular sound, the time duration of the systolic cardiovascular sound, the most dominant frequency component of the sound, the bandwidth of different frequency components, the energy in two frequency bands, the mobility of a part of the signal, the complexity of the signal, the power ratio between different parts of the signal, e.g. two different segments or two different frequency bands, morphological characteristics such as correlation ratios between different segments or amplitude change over time, the number of turning points in a the signal etc. The method could easily be implemented in any kind of data processor unit and therefore be e.g. integrated in a software program to be used by clinicians and doctors when classifying the cardiovascular sound. Furthermore, the method could be integrated in a digital stethoscope, and the stethoscope could therefore be used in order to classify a patient's cardiovascular sound. Since doctors and other clinicians are familiar with a stethoscope, they could easily be taught to use the stethoscope to classify the cardiovascular sound. The result is that the classification could assist the doctor or other clinicians to diagnose whether or not the patient suffers from CAD.

Said at least two signal parameters are in another embodiment extracted from at least two of said number of sub-segments. Hereby the signal parameters used in the multivariate classification method could be extracted from each of the sub-segments, and a large number of the same kind of signal parameters could then be provided and used in the multivariate classification method. This makes the classification of the cardiovascular signal more robust. Further, each sub-segment could be classified in a multivariate classification method.

The at least first signal parameter and/or the at least second signal parameter are in another embodiment being extracted from both said first sub-segment and said second sub-segment. Hereby both the first and the second signal parameter could be extracted from the same sub-sub segments, and the cardiovascular signal could then be classified based on a large number of signal parameters whereby the robustness of the classification is increased.

In another embodiment the method further comprises the step of identifying noisy sub-segments, and discarding said noisy sub-segments prior to said steps of extracting said first signal parameter and/or extracting said second signal parameter. The noisy sub-segments could hereby be discarded before extracting the signal parameters from the sub-segments, and the quality of the extracted signal parameters would hereby be dramatically improved because the sound characteristics influencing the signal parameters would not be influenced by noise. Noisy sub-segments could for instance be sub-segments with a low signal to noise ratio, like sub-segments with friction spikes, sub-segments with background noise or sub-segments with physiological noise like respiration noise. Noisy sub-segments may be identified in different ways, for example as sub-segments with an amplitude, frequency or energy distribution different from the majority of sub-segments.

In another embodiment the method further comprises the step of identifying non stationary sub-segments and the step of discarding said non stationary sub-segments prior to said steps of extracting said first signal parameter and/or extracting said second signal parameter. Non stationary sub-segments could hereby be discarded before extracting the signal parameters from the sub-segments. It is hereby possible to take account of non stationary sound in the diastolic segment, which is often the case because the blood flow in the coronary artery is not constant during a diastole, and the murmurs due to stenosis would therefore not be stationary. Several signal processing methods (e.g. AR-models) assume stationary of the signal to be modeled and error due to non stability could therefore be overcome be dividing the diastolic segment into sub-segments because sub-segments over short time can be assumed to be stationary. Therefore the accuracy of the signal parameters extracted from the AR-models of sub-segments would be more accurate.

In another embodiment of the method at least a part of said first sub-segment is overlapping at least a part of said second sub-segment. The overlapping of segments ensures that as much as possible of the diastolic/systolic segment would be used when extracting the signal parameters and classifying the cardiovascular sound because signal parts without noise could be discarded together with sub-segments comprising a short noise spike. These signal parts would, however, be included in an overlapping segment and thus a larger part of the cardiovascular sound would be used in the extraction of signal parameters and classification of the cardiovascular sound.

The step of classifying the cardiovascular sound comprises in another embodiment the step of calculating the mean value of said first signal parameter and/or said at least second signal parameter extracted from at least two of said number of sub-segments, and using said mean value in said multivariate classification method. The signal parameters used in the classification method could then be calculated as a mean value of signal parameters from a large number of sub-segments and errors due to random noise would then be reduced. The mean value could further be calculated by weighting the different sub-segments differently, for instance such that the sub-segments in the beginning of a diastolic segment would be weighted higher than sub-segments in the end of the diastolic segment. Hereby the beginning of the diastolic segment where murmurs due to stenosis are more audible could have a larger weighting when classifying the cardiovascular sound.

The step of classifying the cardiovascular sound comprises in another embodiment the step of classifying at least one of said number of sub-segments first signal parameter and said second signal parameter in said multivariate classification method, where both said first signal parameter and said second signal parameter are being extracted from said at least one of said number of sub-segments and the step of classifying said cardiovascular sound based on said classifying of said at least one of said number of sub-segments. The cardiovascular sound could then be classified based on a large number of classified sub-segments, and it is hereby possible to determine a probability that the classification is correct. The cardiovascular sound could for instance be considered correct if for instance 99 percent of the sub-segments have been uniformly classified.

In another embodiment the method further comprises the step of modelling at least one of said number of sub-segments and extracting said first signal parameter and/or said second signal parameter from said model. The advantage of using models is that the models could enhance the signal properties, e.g. by using an envelope function or an autoregressive model. Furthermore, models would simplify and optimize the calculation process when the method is implemented in a data processor.

In another embodiment of the method, said first signal parameter and/or said second signal parameter is a frequency level parameter describing a frequency level property of at least one frequency component of at at least one of said number of sub-segments. A frequency level parameter is very useful when classifying cardiovascular sounds because murmurs due to stenosis typically have a dominating frequency component between 200-1200 Hz, and if the most powerful frequency component is inside this interval, it would be a good indication of the presence of murmurs due to stenosis. The frequency level property could also define the ratio between the energy in different frequency bands.

In another embodiment of the method, said first signal parameter and/or said second signal parameter is a complexity parameter describing the complexity of at least one of said number of sub-segments. The complexity of the cardiovascular sound could for instance be defined by the number eigenfunctions used to model the signal, because the more eigenfunctions needed to model the signal the more complex is the signal. The complexity of a cardiovascular sound would typically be maintained and not be influenced by differences from patient to patient. Some eigenfunctions might be attenuated differently from person to person, but they are seldomly removed completely from the cardiovascular sound, and the complexity is therefore maintained.

At least one of said identified diastolic and/or systolic segments is in another embodiment divided into at least 8 sub-segments. The precision of the classification of the cardiovascular sound is hereby improved because the mean value is statistically improved by the square root of the number of samples. The consequence is that a shorter recording of cardiovascular sound is needed in order to classify the sound.

The invention further relates to a system for classifying a cardiovascular sound recorded from a living subject, said system comprises:
  processing means for identifying the diastolic and/or systolic segments of said cardiovascular sound;
  processing means for dividing at least one of said identified diastolic and/or systolic segments into a number of sub-segments comprising at least a first sub-segment and at least a second sub-segment;
  processing means for extracting from said first sub-segment at least a first signal parameter characterizing a first property of said cardiovascular sound, and processing means for extracting from said second sub-segment at least a second signal parameter characterizing to a second property of said cardiovascular sound;
  processing means for classifying said cardiovascular sound using said at least first signal parameter and said at least second signal parameter in a multivariate classification method;
  processing means for classifying said cardiovascular sound using said at least two signal parameters using a multivariate classification method.

Hereby a system for classifying a cardiovascular sound can be constructed and hereby the same advantages as described above are achieved.

The processing means for extracting said first signal parameter and/or said processing means for extracting said second signal parameter are in another embodiment adapted to extract said first signal parameter and/or said second signal parameter from at least one of said number of sub-segments. Hereby the same advantages as described above are achieved.

In another embodiment, the system further comprises processing means for identifying noisy sub-segments and processing means for discarding said noisy sub-segments prior to extracting said first signal parameter and/or extracting said second signal parameter. Hereby the same advantages as described above are achieved.

In another embodiment, the system further comprises processing means for identifying non stationary sub-segments, and processing means for discarding said non stationary sub-segments prior to extracting said first signal parameter and/or extracting said second signal parameter.

The processing means for dividing at least one of said identified diastolic and/or systolic segments into a number of sub-segments is in another embodiment adapted to overlap at least a part of said first sub-segment with at least a part of said second sub-segment. Hereby the same advantages as described above are achieved.

The processing means for classifying said cardiovascular sound is in another embodiment adapted to calculate the mean value of said first signal parameter and/or said at least second signal parameter extracted from at least one of said number of sub-segments and using said mean value in said multivariate classification method. Hereby the same advantages as described above are achieved.

The means for classifying said cardiovascular sound is in another embodiment adapted to classify at least one of said number of sub-segments using said first signal parameter and said second signal parameter in said multivariate classification method and to classify said cardiovascular sound based on said classifying of said at least one of said number of sub-segments. Hereby the same advantages as described above are achieved.

In another embodiment, the system comprises processing means for modelling said at least one of said number of sub-segment processing means for extracting said first signal parameter and/or said second signal parameter from said model. Hereby the same advantages as described above are achieved.

The processing means for extracting said first signal parameter and/or said second signal parameter is in another embodiment adapted to extract at least one frequency level parameter describing a frequency level property of at least one frequency component of at least one of said number of sub-segments. Hereby the same advantages as described above are achieved.

The processing extracting said first signal parameter and/or said second signal parameter is in another embodiment adapted to extract at least one complexity parameter describing the complexity of at least one of said number of sub-segments. Hereby the same advantages as described above are achieved.

The processing means for dividing at least one of said identified diastolic and/or systolic segments into a number of sub-segments is in another embodiment adapted to divide at least one of said identified diastolic and/or systolic segments into at least 8 sub-segments.

The invention further relates to a computer-readable medium having stored therein instructions for causing a processing unit to execute a method as described above. Hereby the same advantages as described above are achieved.

The invention further relates to a stethoscope comprising recording means adapted to record a cardiovascular sound from a living subject, storing means adapted to store said recorded cardiovascular sound, a computer-readable medium and a processing unit, said computer-readable medium having stored therein instructions for causing said processing unit to execute a method as described above and thereby classify said recorded cardiovascular sound. Hereby the method according to the present invention can be implemented in a stethoscope and the above-described advantages are achieved.

The invention further relates to a server device connected to a communication network comprising receiving means adapted to receive a cardiovascular sound recorded from a living subject through said communication network, storing means adapted to store said received cardiovascular sound, a computer-readable medium and a processing unit, said computer-readable medium having stored therein instructions for causing said processing unit to execute a method as described above and thereby classify said received cardiovascular sound. Hereby the method according to the present invention can be implemented in a server connected to a communication network. The server could then perform the above-described method and the above-described advantages are achieved.

In another embodiment of the server, said receiving means are further adapted to receive said cardiovascular sound from a client connected to said communication network. Hereby a clinician/doctor could send a cardiovascular sound to the server using a client device such as a laptop. The server could thereafter classify the received cardiovascular sound. The above-described advantages are hereby achieved.

In another embodiment of the server, the server device further comprises means for sending said classification of said cardiovascular sound to at least one client unit connected to said communication network. Hereby the result of the classification can be sent back to a client, and the clinician/doctor can therefore receive the result of the classification. The above-described advantages are hereby achieved.

DESCRIPTION OF EMBODIMENTS

Figure 1:
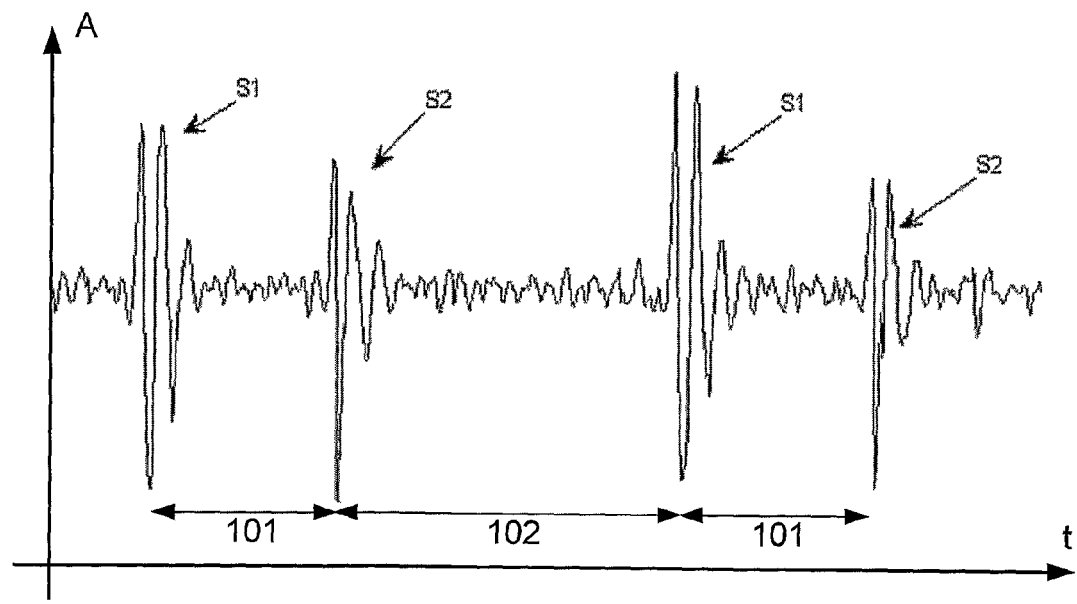
FIG. 1 illustrates a graph of a typical heart sound.

FIG. 1 illustrates a graph of a typical heart sound recorded by a stethoscope and shows the amplitude (A) of the sound pressure at the y-axis and time (t) at the x-axis. The heart sounds reflect events in the cardiac cycle: the deceleration of blood, turbulence of the blood flow and the closing of valves. The closing of the valves is typically represented by two different heart sounds, the first (S1) and the second (S2) heart sound. The first and second heart sounds are illustrated in the figure, and S1 marks the beginning of the systole (101) which is the part of the cardiac cycle in which the heart muscle contracts, forcing the blood into the main blood vessels, and the end of the diastole which is the part of the heart cycle during which the heart muscle relaxes and expands. During diastole (102), blood fills the heart chambers. The duration of systolic segments is nearly constant around 300 ms for healthy subjects. Given a pulse of 60 beats per minute, the duration of a cardiac cycle will be one second in average, and the duration of the diastole will be 700ms. However, the diastolic durations are not constant, but will vary depending on the subject's pulse. In addition, smaller variations of the diastolic duration are introduced due to neural regulations and the effects of respiration.

Figure 2:
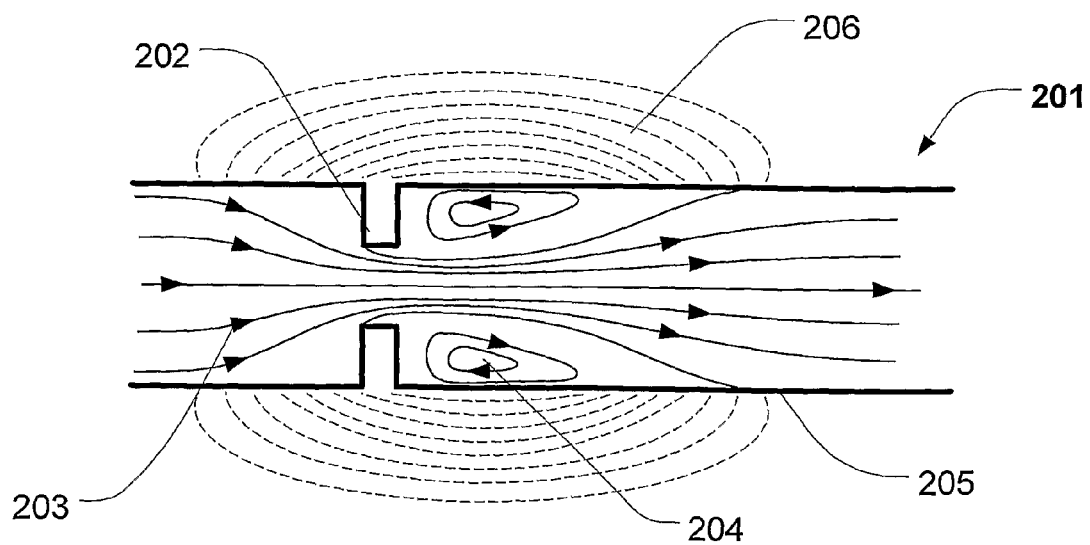
FIG. 2 illustrates a fluid dynamic model of an arterial stenosis.

FIG. 2 illustrates a fluid dynamic model of an arterial stenosis and shows an artery (201) with a stenotic lesion (202). The arrows (203) indicate the blood flow through the artery. Vortices (204) will occur when high velocity blood exits a stenotic lesion (202). These vortices collide with the arterial wall (205) and are transformed into pressure vibrations that cause the arteries to vibrate at their resonance frequencies. The result is that soundwaves in the form of murmers (206) with a frequency corresponding to the arterial wall's resonance frequencies are created and emitted from the arterial wall. Resonance frequencies in the arterial segment are increased if a stenosis is present, and their frequencies depend on the diameter of the stenotic segment compared to the diameter of the artery. As the severity of a stenosis increases, so does the resonance frequency. The resonance frequency of a partial occluded stenotic artery is most likely between 200 Hz and 1100 Hz. The intensity of the vortice fluctuations depends on the blood flow so that murmurs from the left coronary arteries are most intense during diastole, when the blood flow through these arteries is highest. Murmurs from the right coronary arteries are most intense during diastole if there is a stenosis in branches of the right coronary artery supplying the right-sided cavities, whereas the murmur more likely will be systolic from those branches of the right coronary artery giving arterial blood to the left ventricle. The intensity of murmurs not only depends on the blood flow, but also on the frequency content of a murmur. High murmur frequencies are more suppressed by the chest wall compared to low frequencies. The murmurs caused by the arterial vibrations would affect the graph of a heart sound recorded by e.g. a stethoscope.

Figure 3:
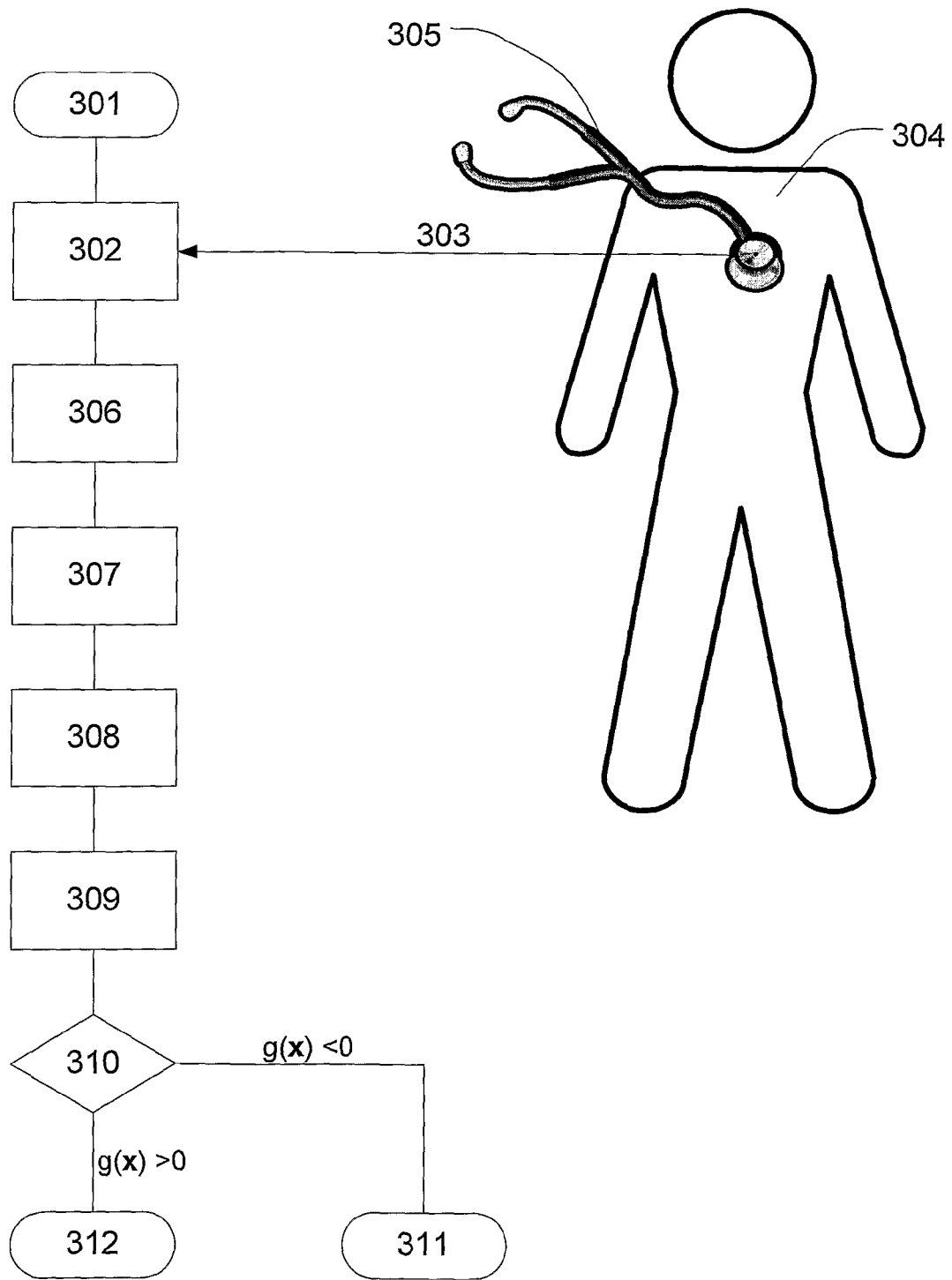
FIG. 3 illustrates an overview in form of a flow diagram of the method according to the present invention.

FIG. 3 illustrates an overview in form of a flow diagram of the method according to the present invention. The method could for instance be implemented as a software program running on a computer or on a microcontroller implemented in a stethoscope. In short, the method starts with an initialization (301), receiving a test signal (302), dividing the test signal into relevant segments (306), filtering the relevant segments (307); calculating/developing a model of the signal (308) in relevant segments; extracting different parameters from the signal and the model (309), performing an analysis of the signal (310) using the extracted parameters and classifying the relevant segments into two groups: one indicating that the signal contains murmurs due to stenosis (311), and one indicating that the signal does not contain murmurs due to stenosis (312).

After the method has been initialized (301) the method receives the test signal (302) as a data file (303). The test signal would be the heart sound from a person (304) recorded and digitalized into a data file, e.g. by a digital stethoscope (305). The test signal would be similar to the heart sound illustrated in FIG. 1; however, the duration of the test signal would typically be 5-15 times longer than the signal shown in FIG. 1. Once the test signal has been received (302), segmentation (306) is performed in order to detect and divide the test signal into segments. The segmentation process would typically detect the heart sounds S1 and S2 and thereafter divide the test signal into systolic and diastolic parts. Hereafter the test signal is filtered (307), and the filtration process includes an autoregressive filter that reduces white noise in the signal and a band pass filter that only lets frequencies between 450-1100 Hz pass. The test signal would thereafter contain the frequencies caused by the vibrations of the arterial wall when stenosis is present in the artery. The autoregressive filter could be implemented as a Kalman filter that is a powerful estimator of past, present and future states, and it can do so even when the precise nature of the modelled system is unknown. This is a desirable feature in the present application when reducing the effects of noise since the exact composition of a murmur is unknown. A first order Kalman filter can reduce the effects of white noise and smooth the noisy heart sound recordings for further processing. The band pass filter could be implemented as a wavelet filter. In another embodiment the Kalman filter is omitted in order to simplify the implementation of the method in e.g. a microprocessor and further to reduce the number of calculations performed by the microprocessor.

When the signal has been filtered (307), relevant segments are selected for further analysis. In one embodiment a part of the diastolic segment is selected for further analysis as the murmur due to stenosis is most likely to be audible in the diastolic segment, and the diastolic segments are in another embodiment also divided into a number of sub-segments in order to remove noise e.g. due to friction between the microphone and the patient's chest (see FIG. 5).

A mathematical model of the signal in the selected segment is hereafter calculated/developed (308) using the sampled heart sound in the data file. The model is used to extract parameters that characterize the sound in the segment and could be used to categorize whether or not the murmurs due to stenosis exist in the sound segment. In the present embodiment an autoregressive all-pole parametric estimation (AR-model) is used to model the signal. In the AR-model the sampled sound signal, y, from the data file is modelled as a linear combination of M past values of the signal and the present input, u, driving the sound generating process. The model can be described by the following equation:

$$y(n) = -\sum_{p=1}^{M} a_p y(n-p) + u(n) \qquad [3.1]$$

where M represents the model order, $A_p$ the AR coefficients and n the sample number. The AR coefficients are determined through an autocorrelation and by minimizing the error associated with the model.

The AR model in this embodiment is used to extract frequency parameters describing the heart sound. A second order model M=2 is preferred because it makes a better separation between the frequency parameters extracted from a heart sound with murmurs present and the frequency parameters extracted from a heart sound with murmurs present.

Thereafter different signal parameters are extracted (309) from the sampled signal and the AR model using signal processing techniques. Some signal parameters could be extracted from the selected segments or sub-segments.

Each signal parameter characterizes the heart sound in the selected segments/sub-segments and could therefore be used to classify the cardiovascular sound, e.g. whether or not murmurs due to stenosis are present in the heart sound.

The signal parameters could for instance be a frequency parameter describing a property in the frequency domain of at least a part of the cardiovascular sound, and the frequency parameter could be used as a parameter in the multivariable classification method described below. Frequency parameters are very good parameters for classifying whether or not murmurs due to stenosis are present in a cardiovascular sound because the stenosis would change the frequency components of the cardiovascular sound. The frequency parameter could for instance be a frequency level parameter describing a frequency level property of at least a part of said cardiovascular sound. The murmurs would typically change the frequency level of the cardiovascular sound, and by using parameters describing the frequency level of the sound a robust classification of the cardiovascular sound could be achieved. The frequency level properties could also characterize the most powerful frequency component of at least a part of said cardiovascular sound. This parameter is a very useful parameter as the murmurs due to stenosis typically have a dominating frequency component between 200-1200 Hz. And if the most powerful frequency component is inside this interval, it would be a good indication of the presence of murmurs due to stenosis. The frequency parameter could also be a frequency bandwidth parameter describing a frequency bandwidth property of at least a part of said cardiovascular sound. The advantage of using a frequency bandwidth property of the cardiovascular sound is that murmurs often have a limited frequency bandwidth, and the frequency bandwidth parameter would therefore be a good indicator of whether or not murmurs due to stenosis are present in the cardiovascular sound. The frequency bandwidth properties could for instance characterize the bandwidth of the most powerful frequency component.

The signal parameters could also be time parameters describing properties in the time domain of at least a part of said cardiovascular sound. By using both time and frequency parameters a very robust classification of the cardiovascular is achieved since time and frequency properties are often uncorrelated. The time parameter could for instance characterize the mobility of at least a part of said cardiovascular sound. The mobility is a good indicator of whether or not murmurs due to stenosis are present in the cardiovascular sound. The mobility describes the variance of the sound, and since murmurs would cause larger variance in the sound, the mobility would be a good indicator.

The signal parameters used in the current embodiment are the number of turnings points per signal length, TP; the mobility of the signal, MB; pole magnitude, PM; normalized AR-peak frequency, NF; and AR spectral ratio, SR.

The number of turning points TP is extracted from the sampled signal in the time domain, and it is found by calculating the number of turns the signal performs in the time domain per unit time. This could be done by determining the amount of local maxima in a time period. Thus:

$$TP = \frac{\text{number of turns}}{\text{signal length}} \quad [3.2]$$

The mobility MB is extracted from the sampled signal in the time domain and found by calculating the variance, $\sigma_y$, of the signal in the time domain and the variance of the signal's first derivative, $\sigma_{y'}$. The mobility is hereafter found by:

$$MB = \frac{\sqrt{\sigma_{y'}^2}}{\sqrt{\sigma_y^2}} = \frac{\sigma_{y'}}{\sigma_y} \quad [3.3]$$

The pole magnitude PM is found by transforming the AR-model into the z-domain and calculating the magnitude of the poles in the z-domain described by the AR-spectrum.

The normalized AR peak frequency NF is based on the assumption that murmurs due to stenosis are more likely to be found in the diastolic segment than in the systolic segment. The NF is found by calculating the angle of the poles in the AR-spectrum in the z-plane and transforming this into a frequency of both a diastolic segment and a systolic segment. If the absolute difference between the two is less than 25 Hz, which is typical in cases where no murmurs due to stenosis are present, then 25Hz is subtracted from the diastolic peak frequency. If the average diastolic frequency is more than 50 Hz greater than the average systolic peak frequency, which is typical when murmurs due to stenosis are present, then 25 Hz is added to the average peak diastolic frequency.

The AR spectral ratio SR is found by calculating the ratio of the energy in the frequency rang 200-500 Hz to the energy in the frequency range 500-1000 Hz of a diastolic segment.

The extracted parameters are thereafter used in a multi-parametric discriminant function in order to classify whether or not the sound segment contains murmurs due to stenosis (310). In this embodiment a linear discriminant function is used to classify the sound segments. The linear discriminant function combines weighted features into a discriminant score g(x) and could be described by:

$$g(x) = w_1 x_1 + w_2 x_2 + w_3 x_3 + \ldots + w_k w_k + w_{i0} = w^T x + w_0 \quad [3.4]$$

where x is the feature vector consisting of the extracted parameters, k represents the number of features, i represents the classes and w is a weight vector that holds the discriminant coefficients. In the case where only two classes must be separated, a single discriminant function is used. A two class classifier is called a dichotomizer. A dichotomizer normally classifies the feature vectors with the decision border g(x)=0 (due to the constant $w_0$). If the discriminant score g(x) is greater than zero, the segment is assigned to class 1, otherwise it is assigned to class 2. Since g is a linear function g(x)=0 it defines a hyperplane decision surface, dividing the multi dimensional space into two half sub spaces. The discriminant score g(x) is the algebraic distance to the hyper-plane. The discriminant function needs to be trained in order to find the weights' values, w, and make a safe and robust classification of the sound segments. The discriminant training procedure needs to be performed before using the system, and the purpose of the procedure is to find the optimal weights values of w so that the hyper plane separates the feature vectors optimally. The training procedure is in one embodiment carried out by using 18 test sounds recorded from 18 test persons where nine test persons have coronary stenosis and nine test persons do not have coronary stenosis. The discriminant training procedure is performed by using the statistical software program SPSS v. 12.0 for windows (SPSS inc., Chicago Ill., USA). The above-mentioned parameters are extracted from the 18 training sounds and used as statistical inputs to the software program. The resulting discriminant could be:

$$g(x) = 164.709 MB - 0.061 NF - 78.027 PM + 27{,}188 SR + 91.878 TP + 33{,}712 \quad [3.15]$$

where MB is the mobility of the signal, NF the AR-peak frequency, PM the pole magnitude, SR the AR spectral ratio and TP the number of turning point.

If the result of the discriminant function is larger than zero (g(x)>0) then the sound segment does not contain murmurs due to stenosis (312). On the other hand, if the discriminant function is smaller than zero (g(x)<0) then the sound segment contains murmurs due to stenosis (311).

The discriminant function could by a person skilled in the art easily be adjusted to include additional or fewer parameters in order to develop a proper discriminant function that can be used to classify the heart sound. Further parameters could for instance be: The Complexity, CP, of the sampled signal in the time domain. This parameter is based on the ratio of the mobility of the first derivative of the signal to the mobility of the signal itself where y" is the second derivative of the filtered heart sound signal. The complexity measure is relatively sensitive to noisy signals since it is based on the second derivative.

$$CP = \frac{MB_{y'}}{MB_y} = \frac{\sigma_{y''}/\sigma_{y'}}{\sigma_{y'}/\sigma_y} \quad [3.6]$$

Other measurements of the signal complexity may be used, for example approximate entropy, spectral entropy or embedding Space Eigen Spectrum.

Further, the AR-peak frequency (PF) could be extracted and used in the discriminant function. The AR-peak frequency could be found by calculating the angle of the AR poles in the z-plane.

Further, a power ratio (PR) can be extracted from the different segments with a power spectral density function (PSD). A PSD can be calculated by the use of a discrete Fourier transform. The power ration can be extracted from the PSD as the energy between 150-350 Hz versus the energy between 350 and 1000 Hz.

The parameters used in the discriminant function could be extracted from different segments of the heart sound, e.g. a number of different diastolic segments where a number of parameters are extracted from each diastolic segment. Thereafter an average value of each parameter could be calculated and used as input in the discriminant function.

Figure 4A:
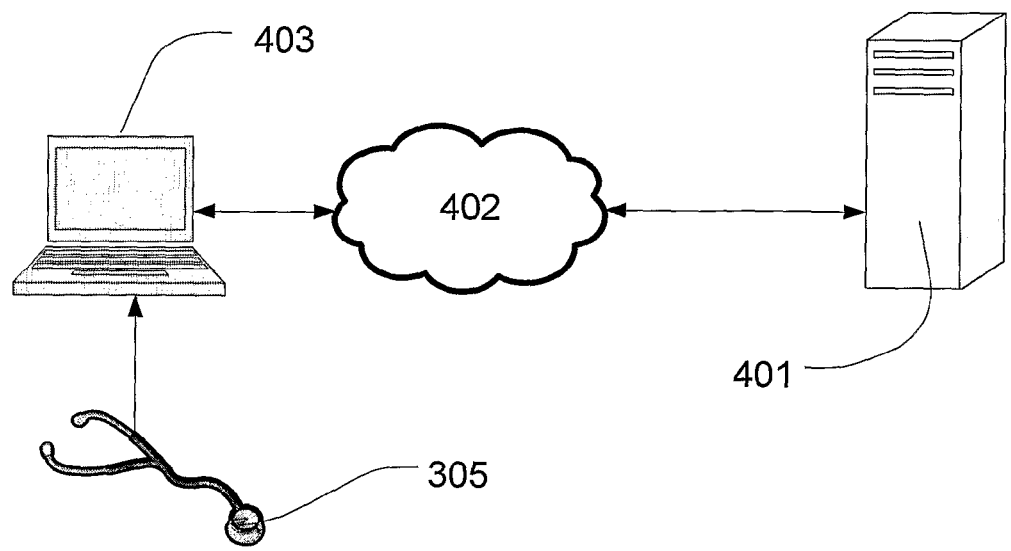
FIG. 4 illustrates an embodiment of the system according to the present invention.
Figure 4B:
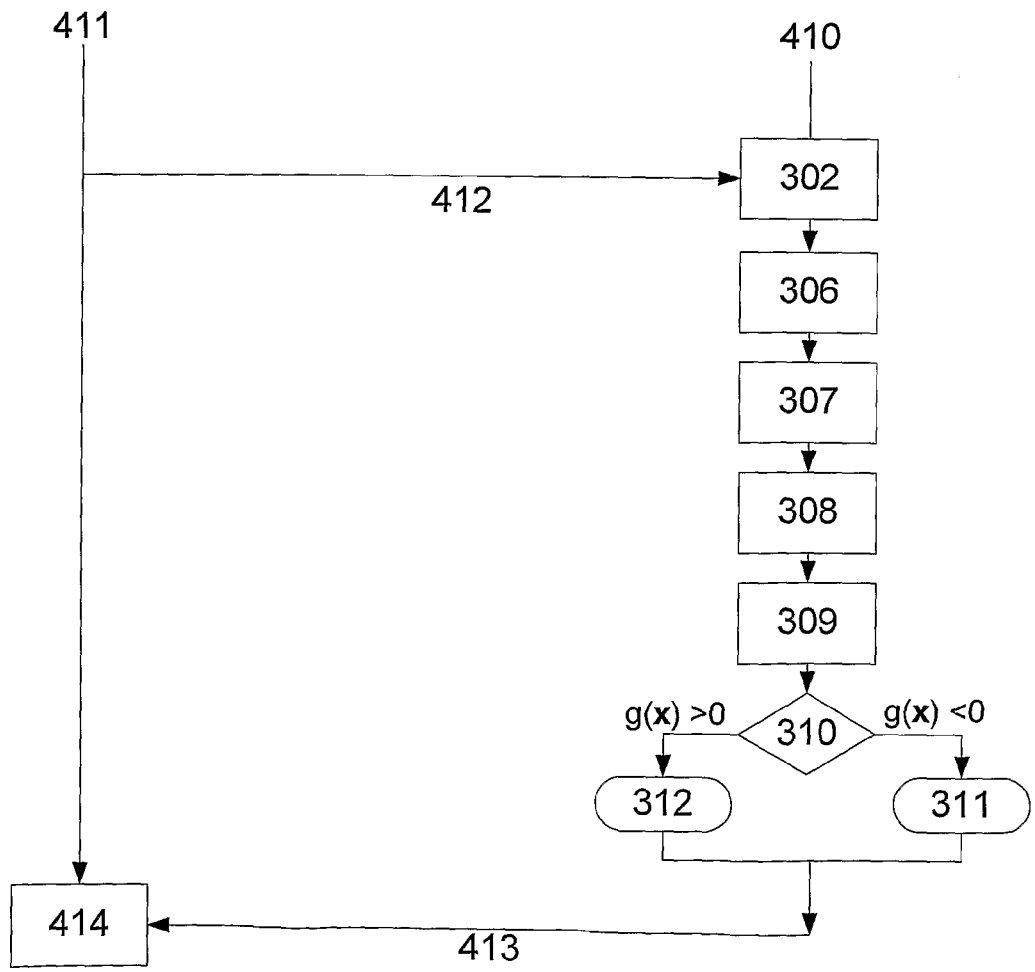

FIG. 4a illustrates an embodiment of the system according to the present invention where a server (401) is programmed to execute the method described in FIG. 3. Furthermore, the server is connected to a network (402), e.g. the Internet and adapted to, on request, receive and analyze heart sound. Clinicians or other medical professionals would record the heart sound from a patient by a digital stethoscope (305) and thereafter transmit the digitalized heart sound to a personal computer (403). The clinician can hereafter send a request to the server in order to have the heart sound analyzed. Once the server has analyzed the heart sound, the result is automatically sent back to the clinician. FIG. 4b illustrates a flow diagram of the process and the communication between the personal computer (403) and the server. The left hand side represents the client side (410) and the right hand side represents the server side (411). First the client sends a heart sound in digital form to the server (412). Thereafter the server performs the method illustrated in FIG. 3 and sends (413) the result of the analysis back to the client where it is displayed (414) to the clinician. The clinician could hereafter evaluate the result in order to choose the right treatment of the patient.

The system according to the present invention could also be implemented as an all in one digital stethoscope. The stethoscope would therefore automatically perform the analysis described in FIG. 3 when a heart sound has been recorded. This means that the method described in FIG. 3 needs to be implemented in stethoscopes' processing means, and the result of the analysis could e.g. be displayed on a small LCD integrated in the stethoscope. An advantage of this embodiment is that most clinicians are familiar with a digital stethoscope and could therefore easily learn to use the stethoscope to diagnose whether or not the patient has a coronary stenosis.

Figure 5:
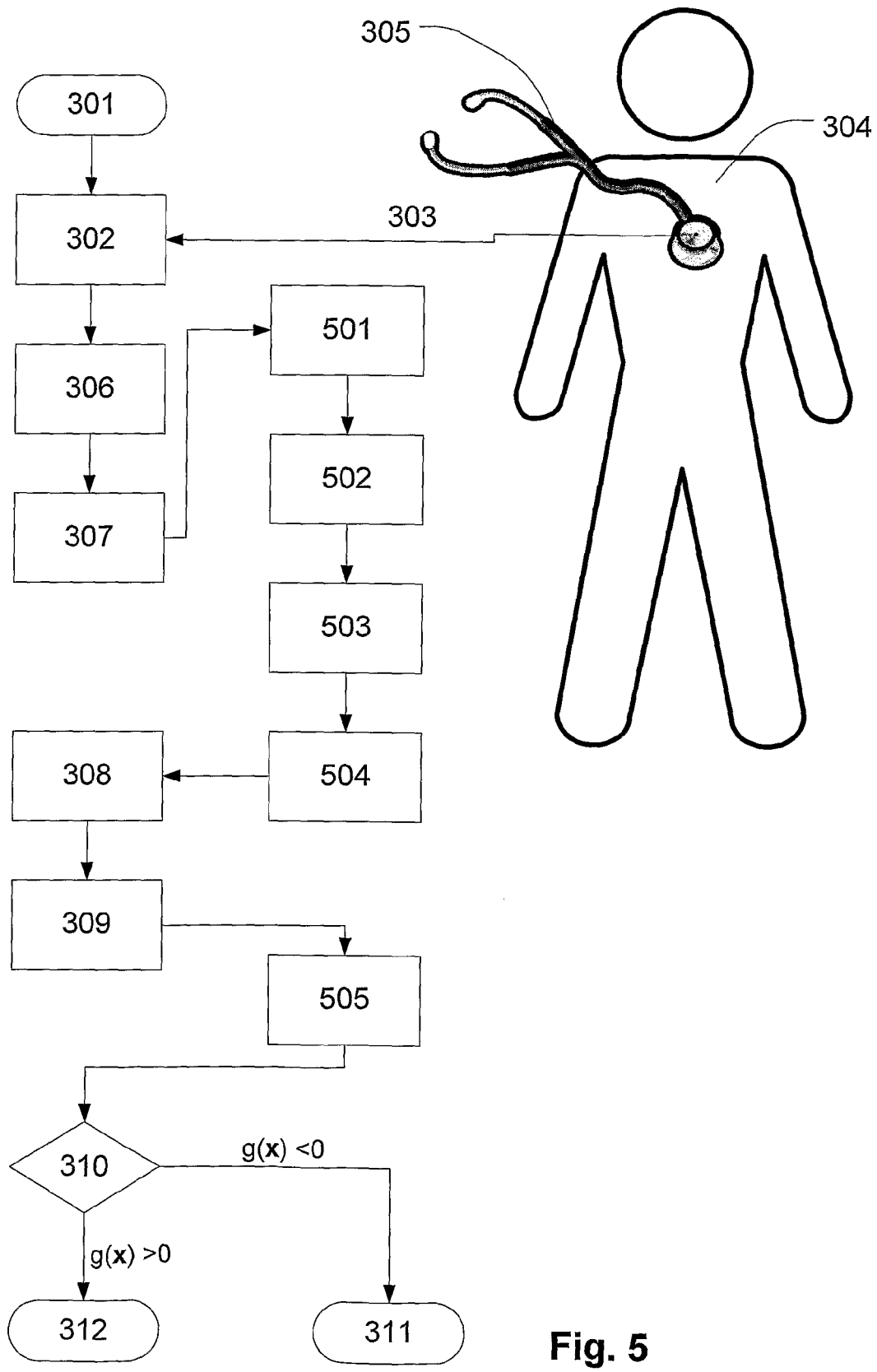
FIG. 5 illustrates another embodiment of the method according to the present invention.

FIG. 5 illustrates another embodiment of the method described in FIG. 3. When the signal has been filtered (307), relevant segments such as systolic and/or diastolic segments are identified (501), and the relevant segments are hereafter divided into sub-segments (502). Noisy sub-segments are in step (503) identified and discarded, and non stationary sub-segments are in step (504) also identified and discarded. In one embodiment a part of the diastolic segment is selected for further analysis as the murmur due to stenosis is most likely to be audible in the diastolic segment. In this embodiment the diastolic segment comprising respiration sounds is discarded in step (501). This is done by calculating the energy level of the diastolic segment in the frequency band 200-440 Hz and comparing this energy level with the median energy level of the entire diastolic segment. The diastolic segment would be discarded if the energy level of the 200-440 Hz frequency band is a factor 1.1 larger than the energy level in the entire diastolic segment.

Figure 9:
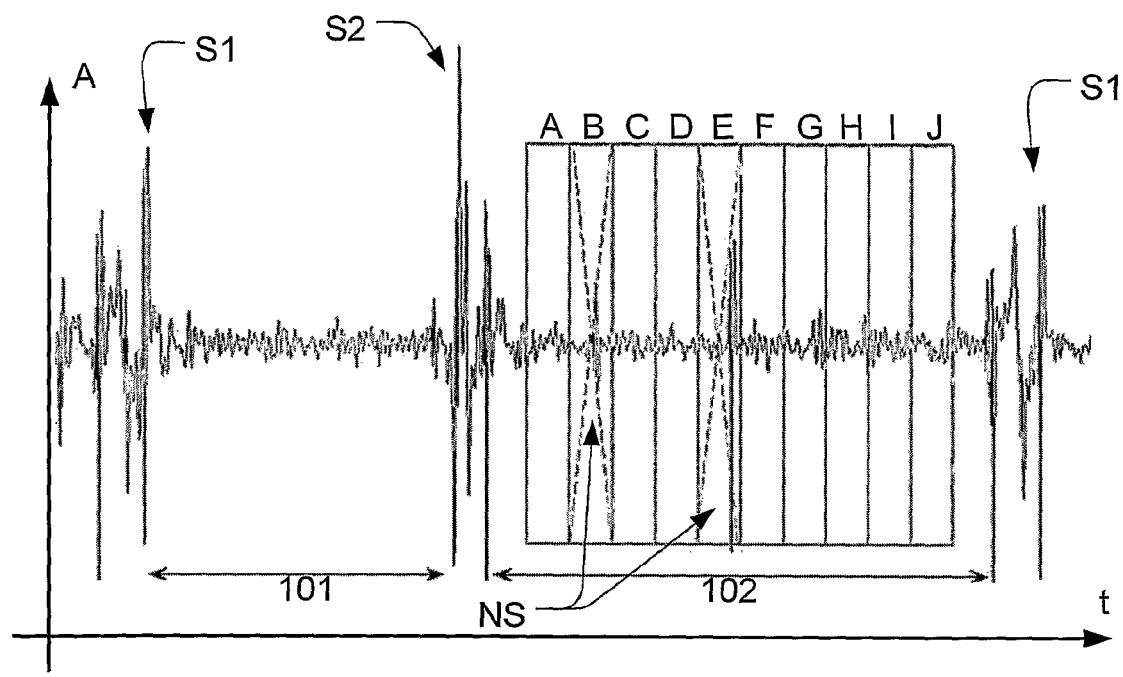
FIG. 9 illustrates how the diastolic segment is divided into a number of subsequent sub-segments.
Figure 10:
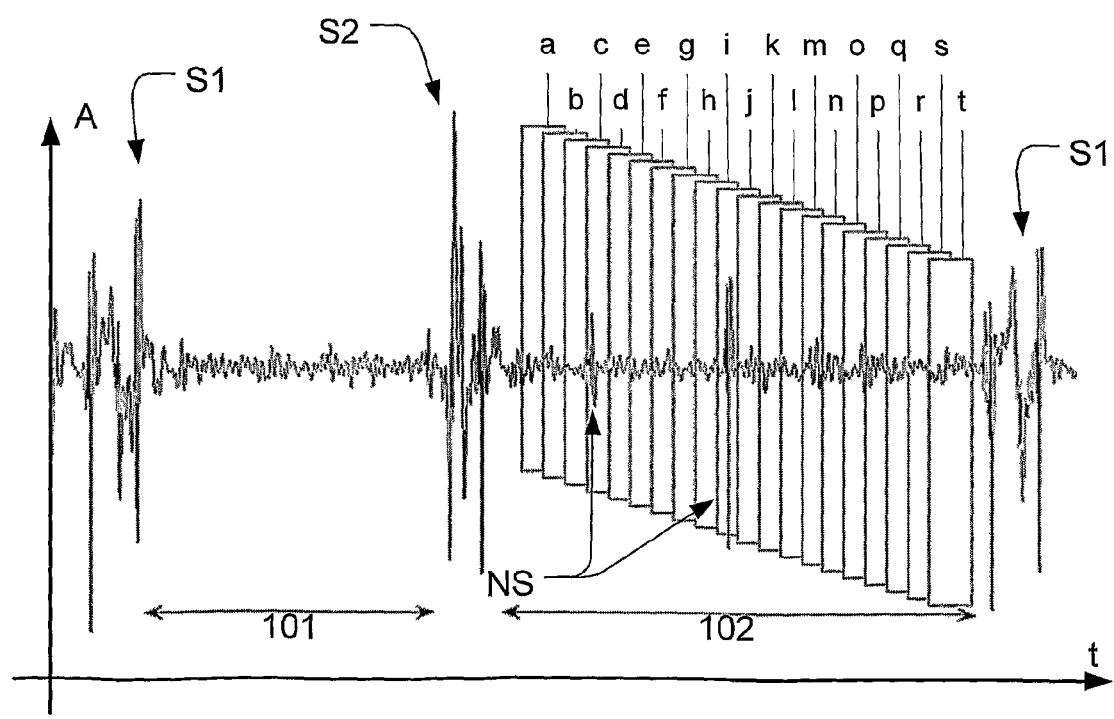
FIG. 10 illustrates how the diastolic segment is divided into overlapping sub-segments.

The remaining diastolic segments are hereafter in step (502) divided into multiple sub-segments and FIGS. 9 and 10 illustrate how a diastolic segment can be divided into sub-segments. FIGS. 9 and 10 illustrate a graph of a typical heart sound recorded by a stethoscope and shows the amplitude (A) of the sound pressure at the y-axis and time (t) at the x-axis. The figures illustrate the first hearth sound (S1), the second hearth sound (S2), a systolic segment (101) and a diastolic segment (102). Two short noise spikes (NS) have been introduced in the diastolic segment. FIG. 9 illustrates how the diastolic segment (102) is divided into a number of subsequent sub-segments (A, B, C, D, E, F, G, J, I, J). Each sub-segment is used in the classification of the cardiovascular sound in step (309) and (310); however, the noisy segments (B) and (E) are due to short noise spikes (NS) discarded in step (503) and therefore not used when classifying the cardiovascular sound.

FIG. 10 illustrates how the diastolic segment (102) is divided into overlapping sub-segments (a, b, c . . . t). It can be seen that at least a part of segment (b) overlaps at least of part of segment (a) and another part of segment (b) overlaps at least a part of segment (c). The remaining segments overlap each other in a similar way. The consequence is that a larger amount of the diastolic segment can be used when classifying the cardiovascular sound in step (309) and (310). Segment (j) is discarded due to a short noise spike (NS), but the last part of segment (j) does not comprise any noise because the duration of sub-segment (j) is larger than the duration of the noise spike. The consequence is that sound suitable for classification of the cardiovascular sound would be discarded when discarding segment (j). However, the part of segment (j) with no noise spikes would be used in the classification as a part of segment (k), since segment (j) and segment (k) overlap each other. The overlapping of segments therefore ensures that as much as possible of the diastolic segment would be used in the classification method.

Figure 11:
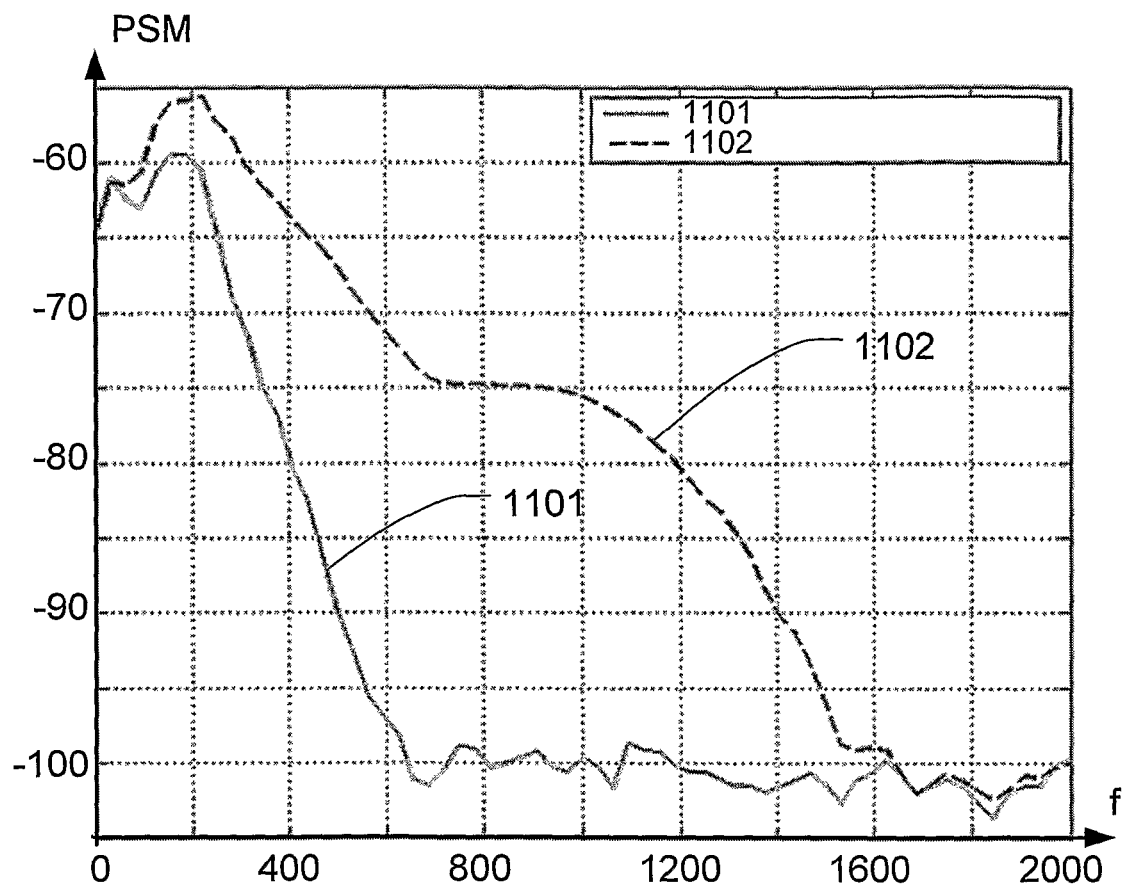
FIG. 11 illustrates the power spectrum density (PSD) for the diastole illustrated in FIG. 9.

Friction spikes often comprise high energy which makes them dominate the signal parameters extracted in step (309). An example of how friction spikes would dominate and influence the value of the signal parameter extracted in step (309) is illustrated in FIG. 11. FIG. 11 illustrates the power spectrum density (PSD) for the diastole illustrated in FIG. 9, where the power spectrum magnitudes (PSM) in dB with (1101) and without (1102) discarding sub-segments containing the friction spikes are plotted as a function of frequency (f) in Hz. Both PSD plots are made by sub-segmenting the signal into sub-segments as illustrated in FIG. 9, then calculating the power spectrum from each sub-segment and then calculating the PSD by averaging the PSD for each sub-segment. The difference between the two graphs (1101) and (1102) is that the 2 sub-segments (B, E) comprising frictions spikes (see FIG. 9) are removed before calculating the average PSD illustrated with the solid line (1101). As seen, friction spikes influence the PSD dramatically in the frequency region 200-1600 Hz. Therefore the removal of short sub-segments with high energy noise can reduce the influence of noise generated by a handhold stethoscope.

The short duration of the sub-segments ensure that only local parts of the signal are excluded. An analysis of heart sound recordings from 20 patients showed that only 44 out of 138 diastoles (32%) included a 256 ms long segment without high energy noise. This indicates that methods like prior art methods using one fixed 256 ms window from each diastole will need to reject 68% of the recorded diastoles, and thereby need recordings more than 3 times longer than the current method to be able to analyze the same number of diastoles.

In the current embodiment the duration of sub-segments is 37.5 ms, but the duration could in other embodiments be shorter or longer than 37.5 ms. and they may also overlap as illustrated in FIG. 10. One advantage in shorter segments is higher resolution in the time domain, and one advantage of longer segments is often better accuracy of parameters calculated from the current sub-segment.

Noisy sub-segments are identified and discarded in step (503) through statistical analyses of the sub-segments. Noisy sub-segments are sub-segments with a low signal to noise ratio, like sub-segments with friction spikes, sub-segments with background noise or sub-segments with physiological noise like respiration noise. Noisy sub-segments may be identified in different ways, for example: sub-segments with an amplitude, frequency or energy distribution different from the majority of sub-segments may be identified as noisy sub-segments.

In the current embodiment the variance of the signal in all sub-segments is calculated and the sub-segments with a variance larger than 1.3 of the median variance of all sub-segments are then discarded. In other embodiments the noisy sub-segments could be identified by filtering the signal into multiple frequency bands and calculating the variance of the frequency bands in each sub-segment. Sub-segments where the variance of one or more frequency bands is larger than the variance of the frequency bands in the remaining sub-segments are considered noisy.

Thereafter in step (504) none stationary sub-segments are removed in order to reduce the influence of non-stationarity. The blood flow in the coronary artery is not constant during a diastole, and the murmurs due to stenosis would therefore not be stationary; however, several signal processing methods like the AR-models assume stationarity of the signal to be modeled. The advantage of using short sub-segments is that the signal over short time can be assumed stationary. This is in the current embodiment done by dividing the sub-segment into sub-sub-segments with a duration of 3.75 ms or 30 samples and then calculate the variance of each sub-sub-segments. Thereby an outline of the variance throughout the sub-segment is constructed. The variance of the outline is then calculated, and the sub-segment is removed if the variance of the outline is larger than 1.

At this point a number of sub-segments have been discarded in order to remove noisy and none stationary sub-segments. This would typically result in 30-100 sub-segments from a cardiovascular recording of approximately 10 seconds.

The remaining sub-segments are thereafter used in step (308) and (309) as described in FIG. 3 in order to extract signal parameters describing different properties of the cardiovascular signal. Thereafter the median of each parameter is calculated using the values of the signal parameter from each sub-segment (505). The median of each parameter is thereafter used in the multiparametric discriminant function as described in FIG. 3. In this embodiment the following signal parameters are used: the mobility, the power-ratio and the pole-amplitude of a 3 pole in an AR model of order 6. Calculating the signal parameter as an average value of signal parameters from many sub-segments reduces the influence of random noise, since the precision of a mean value is statistically improved by the square root of the number of samples.

In order to illustrate the difference between calculating signal parameters from one segment from each diastole versus using multiple sub-segments from all diastoles, the signal parameter PR is calculated for both methods. When analyzing a recording using one 256 ms window for each diastole, the mean PR value calculated over 9 diastoles is 0.484 and the 95% confidence interval of the mean is ±0.0134 (calculated by the stand error multiplied by 1.96). However, if the same recording was analyzed with the current method, using 50 short sub-segments, the 95% confidence interval of the mean value will only be ±0.0064. To reach the same narrow confidence interval using a single segment from each diastole, 39 diastoles are needed, and thereby very long recordings are needed.

The remaining sub-segments are in another embodiment used in order to extract signal parameters describing different properties of the cardiovascular signal and the signal parameters from each sub-segment are thereafter used in the multiparametric discriminant function creating a discriminant score related to each sub-segment. The final discriminant score is then calculated as the median of the scores related to each sub-segments.

Figure 6:
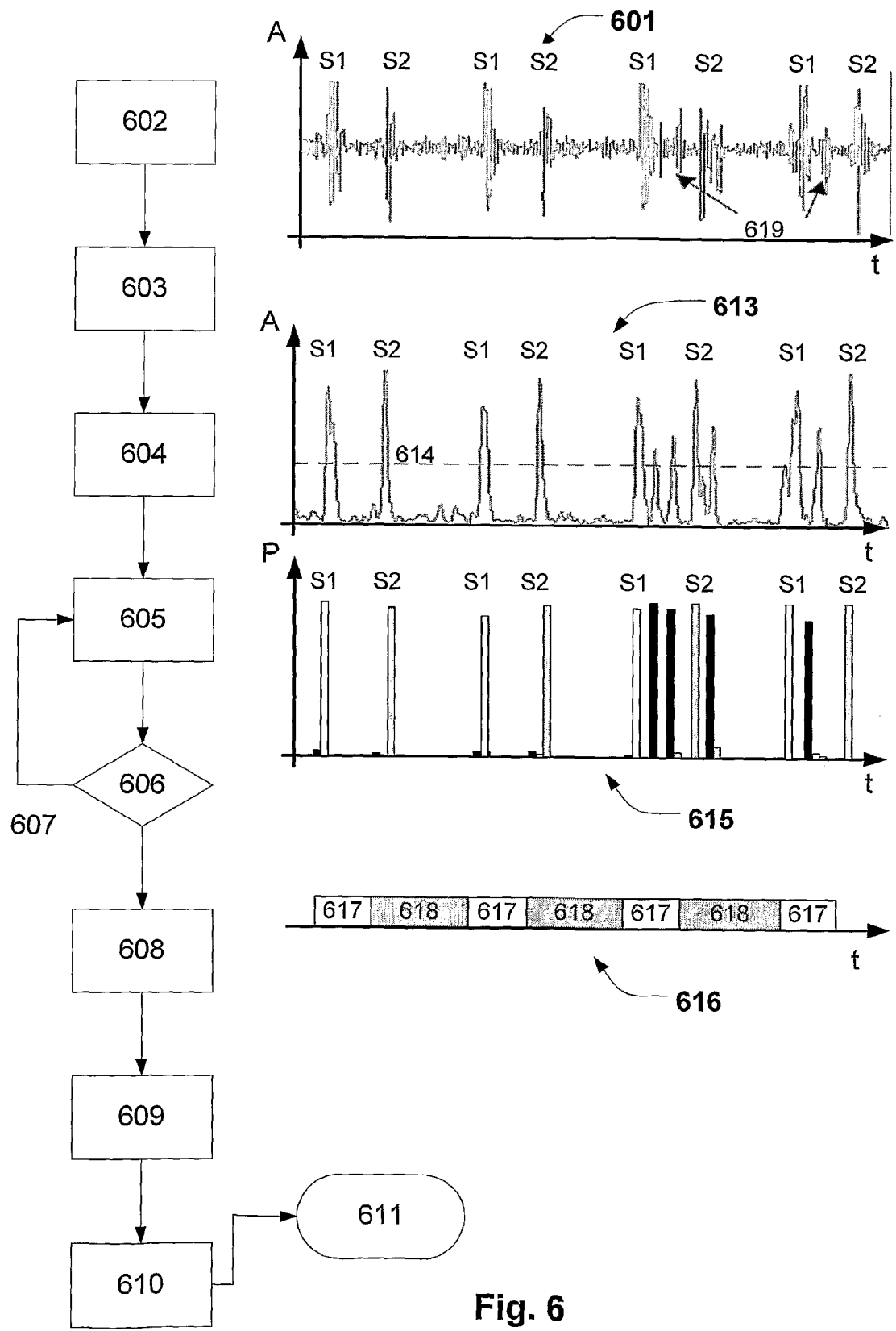
FIG. 6 illustrates a flow diagram of the segmentation method.

FIG. 6 illustrates a flow diagram of the segmentation method (306) according to the present invention used to automatically divide a heart sound (601) into sub-segments. The heart sound (601) has been recorded by a stethoscope, and the signal has been digitized in order to digitally process the signal. The graph shows the amplitude (A) of the sound intensity as a function of time (t). The heart sounds reflect events in the cardiac cycle; the deceleration of blood, turbulence of the blood flow and the closing of valves. The closing of the valves is typically represented by two different heart sounds, the first (S1) and the second (S2) heart sound. The first and second heart sounds are illustrated in the figure, and (S1) marks the beginning of the systole, which is the part of cardiac cycle in which the heart muscle contracts, forcing the blood into the main blood vessels, and the end of the diastole which is the part of the heart cycle during which the heart muscle relaxes and expands. During diastole, blood fills the heart chambers.

The purpose of the segmentation method is to classify the recorded heart sound into systolic, diastolic and noise segments. The illustrated method includes steps of noise reduction (602) followed by envelope creation (603). The noise reduction could be implemented as a high-pass filer followed by removal of high amplitude friction noise spikes due to external noise like movement of the stethoscope during recording and thereafter a low pass filter. The purpose of the envelope creation is to enhance the trend of the signal. The envelope is in this embodiment created by calculating the Shannon energy of the signal:

$$se(n) = -x(n)^2 \cdot \log x(n)^2$$

where x is the signal and se is the Shannon energy. The high amplitude components in the signal are weighted higher than low amplitude components when calculating the Shannon energy. The envelope (613) of the heart sound (601) calculated by using the Shannon energy is shown in figure (613), and it can be seen that the heart sounds S1 and S2 are enhanced.

In order to classify the detected sounds into systolic segments, diastolic segments and noise components based on interval durations on either side of the heart sounds S1 and S2, it is necessary to know how long the intervals between S1's and S2's are. Therefore, the durations of the heart cycles (systolic and diastolic intervals) are extracted from an autocorrelation of the envelope (604). This process is described in detail in FIG. 7.

Candidates S1's and S2's are then detected (605) using the time intervals extracted above and a threshold (614) on the envelope (613). To reduce the number of detected noise spikes, a minimum requirement is applied to the candidate segments, which effectively removes some of the erroneously detected noise spikes. In some recordings there is a big difference between the intensity of S1 and S2 sounds. This causes a problem since some of the low intensity sounds may be missed by the threshold. As a result the segmentation method performs a test for missing S1 and S2 sounds (606). If it can be determined that some segments are missing, the threshold procedure is rerun (607) using lower local thresholds.

Once the signal has been divided into segments as described above interval parameters and frequency parameters for each segment are then extracted (608). The parameters aid in the classification of the sounds into systolic segments and diastolic segments.

The interval parameters are four Boolean parameters extracted for each sound by comparing the time duration to the previous sound and to the next sound with the time intervals extracted using the autocorrelation. The parameters are:

AfterDia: Is true if the sound is succeeded by a second sound after a period corresponding to the duration of a diastole,
AfterSys: Is true if the sound is succeeded by a second sound after a period corresponding to the duration of a systole,
BeforeDia: Is true if the sound follows a second sound after a period corresponding to the duration of a diastole,
BeforeSys: Is true if the sound follows a second sound after a period corresponding to the duration of a systole.

The frequency parameter divides the sounds into low frequency and high frequency sounds by calculating the median frequency of the sound. This is useful information as the first heart sound is expected to be a low frequency sound and the second heart sound is expected to be a high frequency sound.

The parameters are parsed into a Bayesian network where the probability of a segment being a S1, S2 and noise sound is computed (609). The figure illustrates a bar chart (615) of the probability calculated for each sound in the heart signal (601). Each sound would typically have one dominating probability indicating the type (S1, S2 or noise) of the sound. Thereby all sounds are classified into S1, S2 and noise sounds. However, the probability of the three types would in some cases be more or less equal and in such cases it is not possible to classify the sound into a S1, S2 or noise sound using the Bayesian network.

The probabilities are used in the last step (610) to divide and verify the heart signal into systole and diastole segments. This is done by using the position of the identified S1 and S2 sounds to mark the beginning of a systolic and diastolic sound segment respectively The final result of the method (611) is the beginnings and ends of all identified systoles and diastoles. Therefore a "train" (616) of alternating systoles (617) and diastoles (618) can be created. Once the systoles and diastoles have been identified they can be used in further data handling, e.g. to extract further parameters from these segments and thereafter use the parameters to classify the medical condition of the recorded heart sound.

FIG. 7 illustrates the relationship between the envelope autocorrelation and the cardiac cycle, and how the intervals between heart sounds S1 and S2 can be found from the autocorrelation.

Figure 7A:
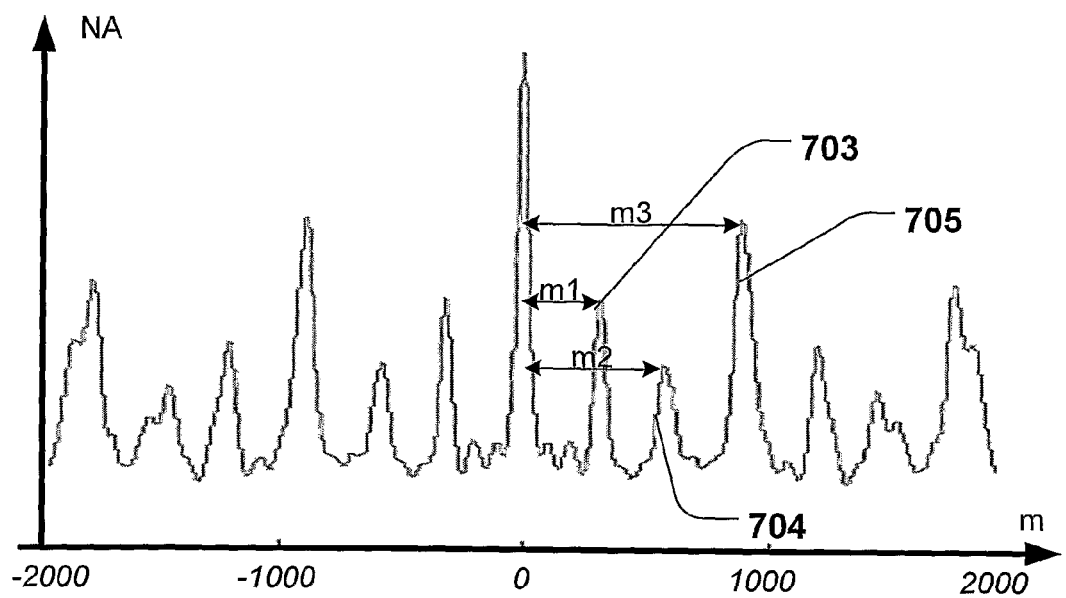
FIG. 7 illustrates, for a heart sound, the relationship between the envelope autocorrelation of a cardiac cycle and the cardiac cycle.

FIG. 7a illustrates the envelope autocorrelation with the normalized autocorrelation at the y-axis (NA) and the displacement (m) of the shifted envelope at the x-axis.

Figure 7B:
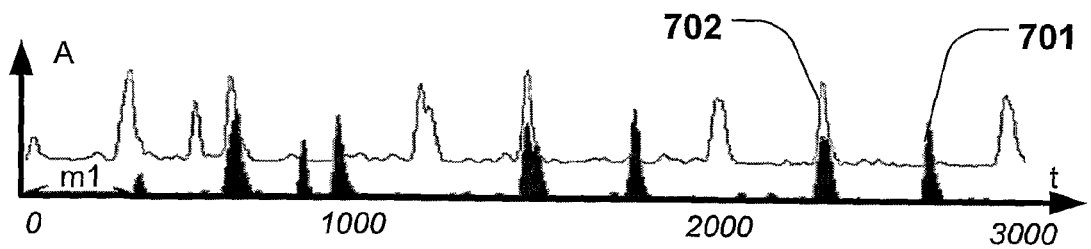

FIG. 7b illustrates the displacement (m1) when the shifted envelope (701) is displaced by the duration of the systole corresponding to the unshifted envelope (702). The y-axis shows the amplitude (A) of the envelope and the x-axis the time (t). The S1's in the displaced envelope are multiplied by the S2's in the unshifted envelopes resulting in the first peak (703) seen in the autocorrelation.

Figure 7C:
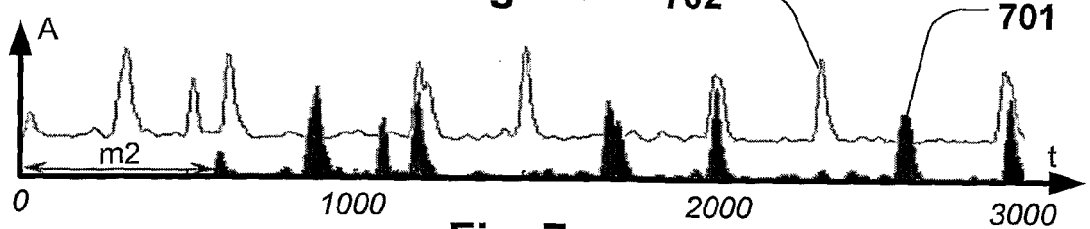
Figure 7D:
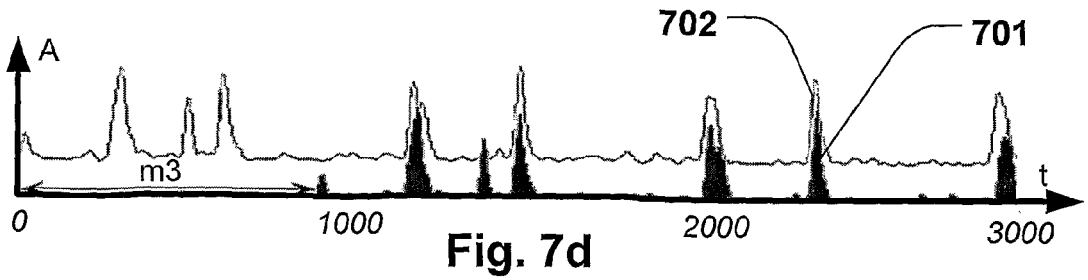

FIG. 7c illustrates the displacement (m2) when the shifted envelope (701) is displaced by the duration of the diastole corresponding to the unshifted envelope (702). The displaced S2's are multiplied by the S1's in the unshifted envelope resulting in the second peak (704) seen in the autocorrelation.

FIG. 6b illustrates the displacement (m3) when the shifted envelope (701) is displaced by the duration of the cardiac cycle corresponding to the unshifted envelope (702). The S1's in the displaced envelope are multiplied by the S1's in the unshifted envelope, and the S2's in the displaced envelope are multiplied by the S2's in the unshifted envelope. When this occurs the dominating peak (705) in the autocorrelation is produced.

The interval between the heart sounds could therefore be found by measuring the distance between the peaks in the autocorrelation as described above.

Figure 8:
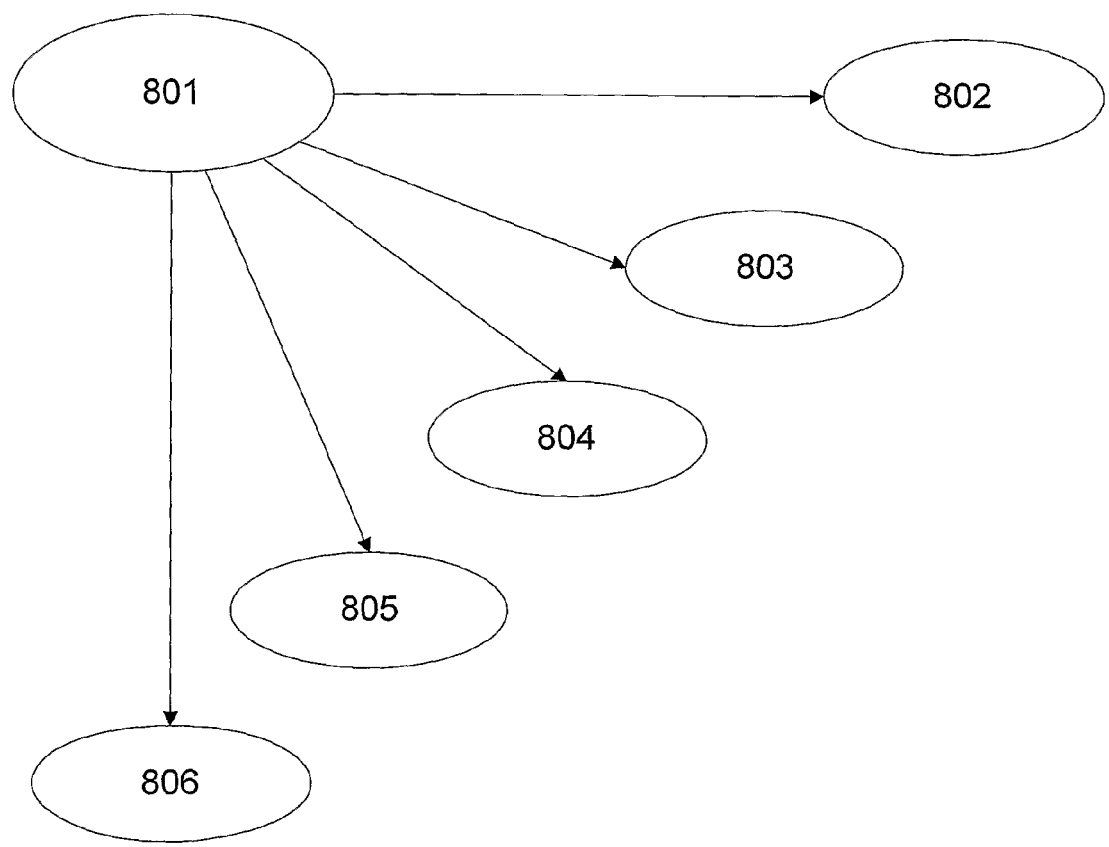
FIG. 8 illustrates the implementation of a Bayesian network used to calculate the probability of a sound being an S1, S2 and noise sound.

FIG. 8 illustrates the implementation of the Bayesian network used to calculate the probability of a sound of being an S1, S2 and noise sound in step (809). The basic concept in the Bayesian network is the conditional probability and the posterior probability. The conditional probability describes the probability of the event a given the event b.

$$P(a|b) = x_c \qquad [8.1]$$

If the above equation describes the initial conditional probability, the posterior probability would be:

$$P(b|a) = x_p \qquad [8.2]$$

According to Bayes' rule the relation between the posterior probability and the conditional probability is:

$$P(b \mid a) = \frac{P(a \mid b)P(b)}{P(a)} \qquad [8.3]$$

where P(a) is the prior probability for the event a, and P(b) is the prior probability for the event b. Equation [8.3] only describes the relation between one parent and one child, but since the event a can be the combination of several events $\{a_1, a_2, \ldots a_n\}$ the equation can be expanded to:

$$P(b \mid a_1, a_2, \ldots, a_n) = \frac{P(a_1, a_2, \ldots, a_n \mid b)P(b)}{P(a_1, a_2, \ldots, a_n)} \qquad [8.4]$$

Since the goal is to find the probability for the different states of b when $a_1$ and $a_2$ are known, $P(a_1, a_2, \ldots a_n)$ is just a normalizing constant k and [7.4] can be simplified to:

$$P(b|a_1, a_2, \ldots a_n) = k \cdot P(a_1, a_2, \ldots a_n|b)P(b) \qquad [8.5]$$

If child events $(a_1, a_2, \ldots a_n)$ are conditionally independent, equation [8.5] can be generalized to:

$$P(b \mid a_1, a_2, \ldots, a_n) = k \cdot P(b) \prod_{i=1}^{N} P(i \mid b) \qquad [8.6]$$

where N is the number of known events a. Equation [8.6] is useful in determining the probability of the event b if the states of all a events are known and if all a events are conditionally independent. A Bayesian network based on equation

[8.6] is called a naive Bayesian network because it requires conditional independency of the children.

The task for the Bayesian network is to evaluate the type of each detected sound above the detection threshold. For each of these sounds, the posterior probability of being an S1 sound, an S2 sound or a noise component is calculated and the Bayesian network is constructed using one parent and five children. The parent is a sound above the envelope threshold (801), and the children are the five parameters described above: Frequency (802), AfterSys (803), AfterDia (804), BeforeSys (805) and BeforeDia (806). When determining the posterior probability for the type of a particular sound, the prior probability for the different states of a sound type P(S) and the conditional probabilities must be known, i.e. the conditional probabilities that "AfterSys" is in a given state when S is a given type, P(AfterSys|S). This posterior probability requires definition of P(S), P(AfterSys|S), P(AfterDia|S), P(BeforeSys|S), P(BeforeDia|S) and P(Frequency|S) before the equation [8.6] can be used to calculate the posterior probability of a sound being a particular type of sound.

The prior probability that a sound is an S1, S2 or a noise component changes between recordings. In the optimal recording, where no noise components are detected, the prior probability for noise is zero, $P(S_{=Noise})=0$. If this is the case and an equal number of S1's and S2's are detected, the prior probability that the detected sound is an S1 is 50%, and similar for S2. Therefore, $P(S_{=S1})=P(S_{=S2})=0.5$ if $P(S_{=noise})=0$. However, this optimal condition cannot be assumed for real signals, and noise sounds would be detected. This will increase the prior probability that a given sound is noise.

The exact probability of a detected sound being noise, $P(S_{noise})$ can be defined if the number of detected noise sounds, $N_{noise}$ and the total number of detected sounds, $N_{sounds}$ are known. For instance, if it is known that four noise sounds are detected, $N_{noise}=4$, and the total number of detected sounds is 20, the probability that the sound being examined is a noise sound is $P(S_{Noise})=4/20$. However, in most signals $N_{noise}$ is unknown and an estimate of $N_{noise}$ is therefore necessary, and this estimate can be based on already available information since the duration of a heart cycle is known from the envelope autocorrelation (804). The expected number of cardiac cycles in one recording can therefore be calculated by dividing the length of the recording with the length of the cardiac cycles. The number of S1's and S2's in a recording is therefore twice the number of cardiac cycles in a recording. The prior probability of the sound type would therefore be:

$$P(S_{=noise}) = \frac{N_{noise}}{N_{sound}} \quad [8.7]$$

and the prior probability that the detected sound is an S1 or S2:

$$P(S_{=s1}) = P(S_{=s2}) = \frac{1 - P(S_{=noise})}{2} \quad [8.8]$$

The conditional probability that an S1 is followed by an S2 sound after an interval corresponding to the duration of a systole, $P(AfterSys|S_{S1})$, depends on several factors. The S1 sounds will normally be followed by S2 sounds after an interval of duration equal to the systole. Deviations from this can also occur, e.g. when S1 is the last sound in the recording, or if S2 is missing because it is not detected by the threshold. It may also occur that a weak (below threshold) S2 is detected because noise occurs in the tolerance window associated with those sounds. The probability that "AfterSys" is false if the sound is an S1 sound may thus be calculated as $$P(\text{AfterSys}_{=false}|S_{=S1})=P(\text{EndSound}\cup\text{Singlesound}, \text{NoiseInWin}) \quad [8.9]$$

where "EndSound" is an event describing that the sound is the last sound in the recording. "SingleSound" describes that S1 is not followed by S2 as the next S2 sound is not detected due to sub-threshold amplitude. "NoiseInWin" describes noise occurrence in the window, where the S2 sound was expected. The conditional probability that "AfterSys" is true given that the examined sound is an S1 sound is given by:

$$P(\text{AfterSys}_{=true}|_{=S1})=1-P(\text{AfterSys}_{=false}|S_{=S1}) \quad [8.10]$$

If the examined sound is an S2 sound it is not likely that any sound occurs after an interval corresponding to the systolic duration since the next S1 sound will occur after the duration of the diastole. An exception is if a noise sound occurs in the window P(NoiseInWin) or if the systole and diastole durations are equal. If the duration of the diastole is equal to the duration of the systole, the S1 sound which follows the S2 sound after the duration of a diastole occurs in both the systole tolerance window and in the diastole tolerance window. This will happen if the heart rate of the subject is high. The probability that a sound occurs in both tolerance windows (overlap) is equal to the degree of the overlap between the systole and diastole tolerance window. This probability is termed P(Overlap). Therefore, the conditional probability that a sound occurs in the window after systole duration if the examined sound is an S2 sound is:

$$P(\text{AfterSys}_{=true}|S_{=S2})=P(\text{Overlap}\cup\text{NoiseInWin}) \quad [8.11]$$

The conditional probability that a sound does not occur after a systole duration, if the examined sound is an S2, is the opposite of the conditional probability that it does occur:

$$P(\text{AfterSys}_{=false}|S_{=S2})=1-P(\text{AfterSys}_{true}|S_{=S2}) \quad [8.12]$$

The conditional probability that a detected noise sound is followed by another sound after the systole duration is based on the probability that a sound of any kind is present in a segment with the length of the used tolerance window. This can be estimated from the ratio of the tolerance window length multiplied by the number of detected sounds minus one to recording length.

$$P(\text{SoundInWin}|S_{=S2})=1-P(\text{AfterSys}_{=true}|S_{=S2}) \quad [8.12]$$

The conditional probability that a detected noise sound is followed by another sound after the systole duration, $P(\text{AfterSys}|S_{=noise})$, is based on the probability that a sound of any kind is present in a segment with the length of the used tolerance window. This can be estimated from the ratio of the tolerance window length multiplied by the number of detected sounds minus one to recording length. The conditional probability that a noise sound is followed by another sound after a systole duration is therefore:

$$P(\text{AfterSys}_{=true} | S_{=noise}) = \quad [8.13]$$

$$P(\text{SoundInWin}) = \frac{(N_{sound}-1) \cdot 2 \cdot Sys_{tol}}{RecLength}$$

where $N_{sound}$ is the number of sounds within the recording, $Sys_{tot}$ is the duration of a systole and RecLength is the length of the recording. The conditional probability that a noise is not followed by another sound after the systole interval is the opposite:

$$P(\text{AfterSys}_{false}|S_{=noise}) = 1 - P(\text{SoundInWin}) \quad [8.14]$$

The conditional probabilities for P(AfterDia|S), P(BeforeSys|S) and P(BeforeDia|S) are based on the same assumptions used to define P(AfterSys|S). These conditional probabilities can be found in the tables below:

| | P(AfterSys|S) | |
|---|---|---|
| | False | True |
| S1 | P((EndSound ∪ SingleSound), NoiseInWin) | 1 − P((EndSound ∪ SingleSound), NoiseInWin) |
| S2 | 1 − P(Overlap ∪ NoiseInWin) | P(Overlap ∪ NoiseInWin) |
| Noise | 1 − P(SoundInWin) | P(SoundInWin) |

| | P(AfterDia|S) | |
|---|---|---|
| | False | True |
| S1 | 1 − P(Overlap ∪ NoiseInWin) | P(Overlap ∪ NoiseInWin) |
| S2 | P((EndSound ∪ SingleSound), NoiseInWin | 1 − P((EndSound ∪ SingleSound), NoiseInWin) |
| Noise | 1 − P(SoundInWin) | P(SoundInWin) |

| | P(AfterSys|S) | |
|---|---|---|
| | False | True |
| S1 | 1 − P(Overlap ∪ NoiseInWin) | P(Overlap ∪ NoiseInWin) |
| S2 | P((EndSound ∪ SingleSound), NoiseInWin | 1 − P((EndSound ∪ SingleSound), NoiseInWin) |
| Noise | 1 − P(SoundInWin) | P(SoundInWin) |

| | P(AfterDia|S) | |
|---|---|---|
| | False | True |
| S1 | P((EndSound ∪ SingleSound), NoiseInWin) | 1 − P((EndSound ∪ SingleSound), NoiseInWin) |
| S2 | 1 − P(Overlap ∪ NoiseInWin) | P(Overlap ∪ NoiseInWin) |
| Noise | 1 − P(SoundInWin) | P(SoundInWin) |

It has previously been found that the frequency parameter classified 86% of the S1 sounds as low frequent and 80% of the S2 sounds as high frequent. 85% of all noise sounds were classified as high frequent. This information was used as the conditional probabilities between the frequency parameter P(Frequency|S):

| | P(Frequency|S) | |
|---|---|---|
| | Low | High |
| S1 | 0.86 | 0.14 |
| S2 | 0.20 | 0.80 |
| Noise | 0.15 | 0.85 |

When all conditional probabilities are found, equation [8.6] is used by the Bayesian network to calculate the posterior probabilities for all detected sounds. This way, three probabilities are calculated for each sound that reflect how likely it is that the current sound is a given type.

It should be noted that the above-mentioned embodiments rather illustrate than limit the invention, and that those skilled in the art will be able to suggest many alternative embodiments without departing from the scope of the appended claims.

The invention claimed is:

1. A method of classifying a cardiovascular sound recorded from a living subject, said method comprises the steps of:

identifying diastolic and/or systolic segments of said cardiovascular sound;

dividing at least one of said identified diastolic and/or systolic segments into a number of sub-segments comprising at least a first sub-segment and at least a second sub-segment;

identifying noisy sub-segments;

discarding said noisy sub-segments;

extracting from said first sub-segment at least a first signal parameter characterizing a first property of said cardiovascular sound, extracting from said second sub-segment at least a second signal parameter characterizing a second property of said cardiovascular sound, wherein said first and second sub-segments from which said at least first and second signal parameters are respectively extracted are from the same diastolic or systolic segment; and classifying said cardiovascular sound using said at least first signal parameter and said at least second signal parameter using a multiparametric discriminate function.

2. A method according to claim 1, wherein said at least first signal parameter and/or said at least second signal parameter are being extracted from at least two of said number of sub-segments of the same diastolic or systolic segment.

3. A method. according to claim 2, wherein said step of classifying said cardiovascular sound comprises the step of:
calculating the mean value of said at least first signal parameter and/or said at least second signal parameter extracted from at least two of said number of subsegments of the same diastolic or systolic segment, and using said mean value in said multiparametric discriminate function.

4. A method according to claim 2, wherein said step of classifying said cardiovascular sound comprises the steps of:
classifying at least one of said number of sub-segments using said at least first signal parameter and said at least second signal parameter using said multiparametric discriminate function, where both said at least first signal parameter and said at least second signal parameter are in being extracted from said at least one of said number of sub-segments, and
classifying said cardiovascular sound based on said classifying of said at least one of said number of subsegments.

5. A method according to claim 1, wherein said method further comprises the steps of:
identifying non stationary sub-segments, and
discarding said non stationary sub-segments prior to said steps of extracting said at least first signal parameter and/or extracting said at least second signal parameter.

6. A method according to claim 1, wherein at least A part of said first sub-segment is overlapping at least a part of said second sub-segment.

7. A method according to claim 1, wherein said method further comprises the steps of modelling at least one of said number of sub-segments and extracting said at least first signal parameter and/or said at least second signal parameter from said model.

8. A method according to claim 1, wherein said at least first signal parameter and/or said at least second signal parameter is a frequency level parameter describing a frequency level property of at least one frequency component of at least one of said number of sub-segments.

9. A method according to claim 1, wherein said at least first signal parameter and/or said at least second signal parameter are complexity parameters describing the complexity of at least one of said number of sub-segments.

10. A method according to claim 1, wherein at least one of said identified diastolic and/or systolic segments is divided into at least 8 sub-segments.

11. A computer-readable medium having stored therein instructions for causing a processing unit to execute a method according to claim 1.

12. A server device connected to a communication network comprising:
receiving means adapted to receive a cardiovascular sound recorded from a living subject through said communication network,
storing means adapted to store said received cardiovascular sound, and
a computer-readable medium and a processing unit, said computer-readable medium having stored therein instructions for causing said processing unit to execute a method according to claim 1 and thereby classify said received cardiovascular sound.

13. A server device according to claim 12, wherein said receiving means are further adapted to receive said cardiovascular sound from a client connected to said communication network.

14. A server device according to claim 12, wherein said server device further comprises means for sending said classification of said cardiovascular sound to at least one client unit connected to said communication network.

15. A system for classifying a cardiovascular sound recorded from a living subject, said system comprising:
processing means for identifying the diastolic and/or systolic segments of said cardiovascular sound;
processing means for dividing at least one of said identified diastolic and/or systolic segments into a number of sub-segments comprising at least a first sub-segment and at least a second sub-segment;
processing means for identifying noisy sub-segments;
processing means for discarding said noisy sub-segments;
processing means for extracting from said first sub-segment at least a first signal parameter characterizing a first property of said cardiovascular sound, and processing means for extracting from said second sub-segment at least a second signal parameter characterizing a second property of said cardiovascular sound, wherein said first and second sub-segments from which said at least first and second signal parameters are respectively extracted from the same diastolic or systolic segment;
processing means for classifying said cardiovascular sound using said at least first signal parameter and said at least second signal parameter using a multiparametric discriminate function.

16. A method according to claim 15, wherein said processing means for extracting said at least first signal parameter and/or said processing means for extracting said at least second signal parameter is adapted to extract said at least first signal parameter and/or said at least second signal parameter from at least two of said number of sub-segments of the same diastolic or systolic segment.

17. A. system according to claim 16, wherein said processing means for classifying said cardiovascular sound is adapted to calculate the mean value of said at least first signal parameter and/or said at east second signal parameter extracted from at least two of said number of sub-segments of the same diastolic or systolic segment, and using said mean value in said multiparametric discriminate function.

18. A system according to claim 16, wherein said means for classifying said cardiovascular sound is adapted to classify at least one of said number of sub-segments using said at least first signal parameter and said at least second signal parameter using said multiparametric discriminate function and to classify said cardiovascular sound based on said classifying of said at least one of said number of sub-segments.

19. A system according to claim 15, wherein said system further comprises:
processing means for identifying the non stationary sub-segments, and
processing means for discarding said non stationary sub-segments prior to extracting said at least first signal parameter and/or extracting said at least second signal parameter.

20. A system according to claim 15, wherein said processing means for dividing at least one of said identified diastolic and/or systolic segments into a number of sub segments is adapted to overlap at least a part of said first sub-segment with at least a part of said second sub-segment.

21. A system according to claim 16, wherein said system further comprises processing means for modelling at least one of said number of sub-segments and processing means for extracting said at least first signal parameter and/or said at least second signal parameter from said model.

22. A system according to claim 15, wherein said processing means for extracting said at least first signal parameter and/or said at least second signal parameter is adapted to extract at least one frequency level parameter describing a frequency level property of at least one frequency component of at least one of said number of sub-segments.

23. A system according to claim 15, wherein said processing means for extracting said at least first signal parameter and/or said at least second signal parameter is adapted to extract at least one complexity parameter describing the complexity of at least one of said number of sub-segments.

24. A system according to claim 15, wherein said processing means for dividing at least one of said identified diastolic and/or systolic segments into a number of identified diastolic and/or systolic segments into at least a 8 sub-segments.

25. A stethoscope comprising:
recording means adapted to record a cardiovascular sound from a living subject,
storing means adapted to store said recorded cardiovascular sound, and
a computer-readable medium and a processing unit, said computer-readable medium having stored therein instructions for causing said processing unit to execute a method according to claim 1 and thereby classify said recorded cardiovascular sound.

* * * * *